(12) United States Patent  (10) Patent No.: US 8,342,887 B2
Gleason et al.  (45) Date of Patent: Jan. 1, 2013

(54) IMAGE GUIDE WIRE CONNECTION (75) Inventors: Kenneth R. Gleason, Harrisburg, PA (US); Keith Edwin Miller, Manheim, PA (US); Kenneth Alan McGiboney, Gilbert, AZ (US); Laurence Alan Daane, Portland, OR (US)

(73) Assignee: Tyco Electronics Corporation, Berwyn, PA (US)

( * ) Notice: Subject to any disclaimer, the term of this patent is extended or adjusted under 35 U.S.C. 154(b) by 0 days.

(21) Appl. No.: 13/208,863

(22) Filed: Aug. 12, 2011

(65) Prior Publication Data

US 2011/0294358 A1 Dec. 1, 2011

Related U.S. Application Data (63) Continuation of application No. 12/427,799, filed on Apr. 22, 2009, now abandoned.

(51) Int. Cl.
H01R 24/04 (2006.01)
(52) U.S. Cl. .......................... 439/668; 439/669; 439/909
(58) Field of Classification Search .................. 439/668, 439/669, 909; 607/115
See application file for complete search history.

(56) References Cited

U.S. PATENT DOCUMENTS

| 4,815,471 | A | 3/1989 | Stobie |
| 5,348,481 | A | 9/1994 | Ortiz |
| 5,358,409 | A | 10/1994 | Obara |
| 5,413,508 | A | 5/1995 | Obara |
| 6,162,101 | A | 12/2000 | Fischer et al. |
| 6,428,336 | B1 | 8/2002 | Akerfeldt |
| 6,663,570 | B2 | 12/2003 | Mott et al. |
| 6,741,892 | B1 | 5/2004 | Meadows et al. |
| 6,913,478 | B2 | 7/2005 | Lamirey |
| 7,108,549 | B2 | 9/2006 | Lyu et al. |
| 7,241,180 | B1 | 7/2007 | Rentas Torres |
| 7,244,150 | B1 | 7/2007 | Brase et al. |
| 7,274,956 | B2 | 9/2007 | Mott et al. |
| 7,326,088 | B2 | 2/2008 | Tulkki |
| 7,347,751 | B2 | 3/2008 | Sweeney et al. |
| 7,364,479 | B1 | 4/2008 | Deily |
| 7,648,401 | B2 | 1/2010 | Guenther et al. |
| 2002/0095079 | A1* | 7/2002 | Putz .............................. 600/378 |
| 2003/0021557 | A1 | 1/2003 | Eichelberger et al. |
| 2003/0023164 | A1 | 1/2003 | Eichelberger et al. |
| 2004/0082866 | A1* | 4/2004 | Mott et al. .................... 600/486 |

FOREIGN PATENT DOCUMENTS

| EP | 1654980 A1 | 5/2006 |
| WO | WO-00/56402 A | 9/2000 |
| WO | WO-02/40088 A2 | 5/2002 |
| WO | WO-03/061469 A1 | 7/2003 |

OTHER PUBLICATIONS

International Search Report for International Application No. PCT/US2010/001048.

* cited by examiner

Primary Examiner — Hien Vu (57) ABSTRACT

An electrical connector and assembly having a body arranged and disposed to receive an interconnector of a guide wire at a first end and an interface cable at a second end, and a contact module in the body, the contact module comprising a contact housing and a plurality of contacts, disposed in the contact housing, the plurality of contacts being configured for electrical connection with the interface cable and the guide wire, is disclosed.

4 Claims, 11 Drawing Sheets

IMAGE GUIDE WIRE CONNECTION

CROSS-REFERENCE TO RELATED APPLICATIONS

This application is continuation of copending, commonly assigned U.S. application Ser. No. 12/427,799, filed Apr. 22, 2009, the disclosure of which is incorporated herein by reference.

FIELD

The present disclosure is directed to an electrical connector assembly. In particular, the present disclosure is directed to an assembly for connecting an imaging guide wire to an electronic monitoring and control box.

BACKGROUND

Electronic medical devices permitting measurement of internal conditions of a human body are well known. Often, these electronic medical devices are connected to monitoring and control devices and systems. For safety, sanitation, convenience, and effectiveness, the connection of the monitoring and control devices to these medical devices is performed by electrically connecting a cable extending from the monitoring and control device to a cable extending from the medical device.

Known connectors do not adequately connect with certain types of medical devices, such as catheters. Catheters may include hypo tubes, which may include delicate portions with dielectric and conductive portions. These hypo tubes may be as thin as about $14/1000$ of an inch. Known connectors may break these hypo tubes or may be unreliable in separating the electrical signals transmitted to the various conductive portions.

Therefore, there is an unmet need to provide an electrical connector and an electrical connector assembly permitting rotation, able to interface with cables and to work in conjunction with hypo tubes.

SUMMARY OF THE DISCLOSURE

This disclosure provides an electrical connector and electrical connector assembly permitting rotation that is configured to interface with cables and to work in conjunction with hypo tubes.

According to an embodiment, an electrical connector includes a body arranged and disposed to receive an interconnector of a guide wire at a first end and an interface cable at a second end, and a contact module in the body, the contact module comprising a contact housing and a plurality of contacts, disposed in the contact housing, the plurality of contacts being configured for electrical connection with the interface cable and the guide wire. In the embodiment, the interconnector comprises a plurality of axial conductive portions separated by a plurality of axial dielectric portions, the number of the axial conductive portions corresponding to the number of the contacts in the contact module, and the interface cable is arranged and disposed for electrically connecting with a monitoring and control device.

According to another embodiment, an electrical connector assembly includes a guide wire having an interconnector, the interconnector comprising a plurality of axial conductive portions separated by a plurality of axial dielectric portions, the number of the axial conductive portions corresponding to the number of the contacts in the contact module, the guide wire further comprising a sensor at a distal end of the guide wire, the sensor arranged and disposed for measuring internal conditions of a human; an interface cable, the interface cable arranged and disposed for electrically connecting with a monitoring and control device; and an electrical connector connecting the guide wire to the interface cable. In the embodiment, the connector comprises a body, and a contact module, the contact module comprising a contact housing and a plurality of contacts disposed in the contact housing for electrical connection with the interface cable and the guide wire. The body is arranged and disposed for protecting internal components of the electrical connector.

According to yet another embodiment, an electrical connector includes a body arranged and disposed to receive a contact module and arranged and disposed to receive a hypo tube of a guide wire at a first end and an interface cable at a second end, the contact module, and a cam actuator and a cam. In the embodiment, the contact module includes a contact housing and a plurality of contacts, the contact housing arranged and disposed for receiving the plurality of contacts, the plurality of contacts being configured for electrical connection with the interface cable and the guide wire. The cam actuator is arranged and disposed for partially rotating the cam, the cam being arranged and disposed for engaging the contacts upon being partially rotated, thereby permitting the interconnector to be inserted into the contact module. The hypo tube comprises a plurality of axial conductive portions and a plurality of axial dielectric portions, and the interface cable is arranged and disposed for electrically connecting with a monitoring and control device.

An advantage of the present disclosure is permitting rotational movement of a catheter thereby permits physicians to have increased ability for manipulating medical devices.

Another advantage of the present disclosure is that the assembly allows longer cables to be used with medical devices.

Yet another advantage of the present disclosure is the interoperability of the connector with hypo tubes.

Still yet another advantage of the present disclosure is the decreased production cost of the connector.

Further aspects of the system and apparatus are disclosed herein. The features as discussed above, as well as other features and advantages of the present disclosure will be appreciated and understood by those skilled in the art from the following detailed description and drawings.

BRIEF DESCRIPTION OF THE DRAWINGS

Wherever possible, the same reference numbers will be used throughout the drawings to represent the same parts.

DETAILED DESCRIPTION

Figure 1:
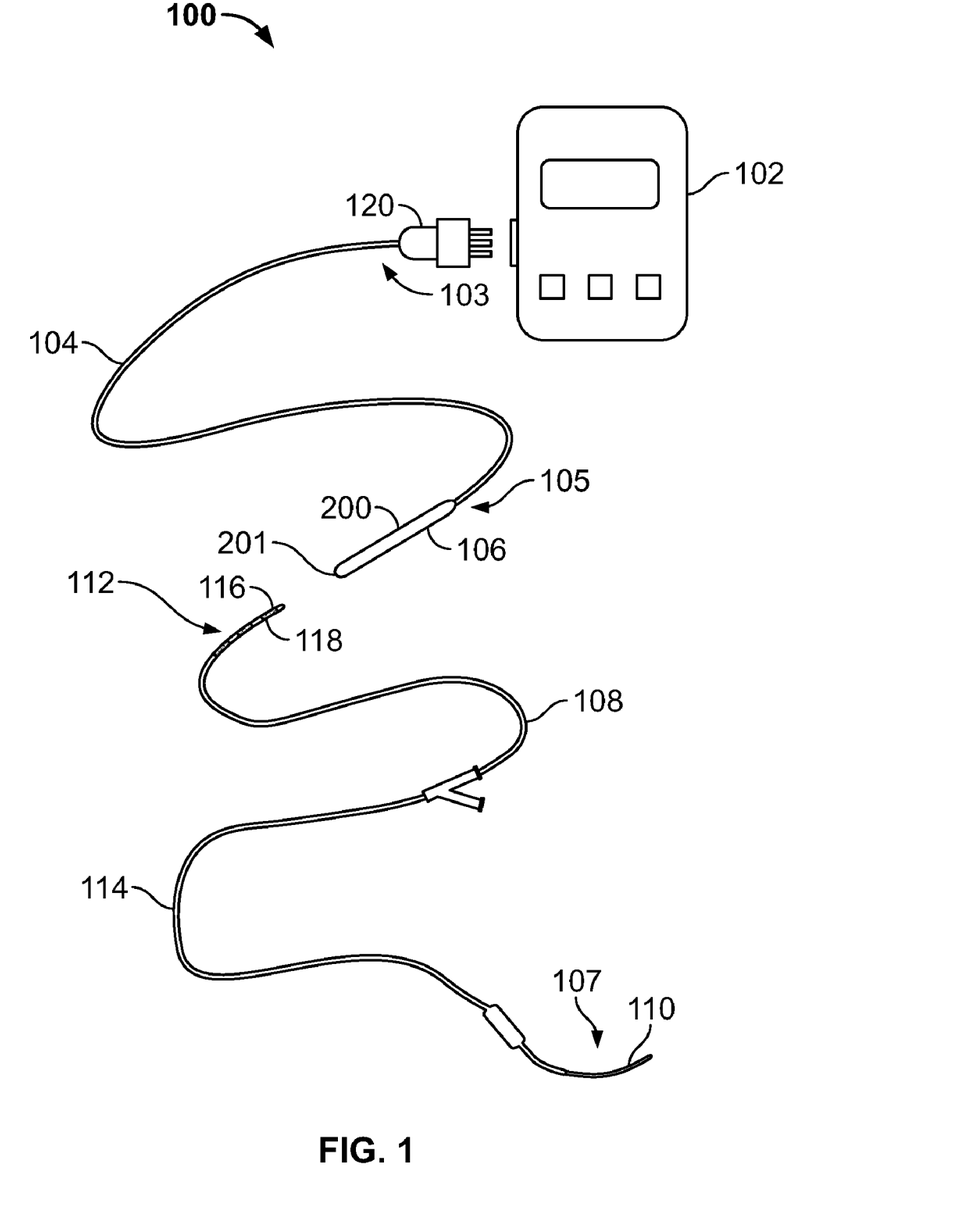
FIG. 1 illustrates a schematic diagram of an exemplary embodiment of a guide wire assembly according to the disclosure.

FIG. 1 illustrates an exemplary embodiment of a guide wire assembly 100. Guide wire assembly 100 includes a monitoring and control device 102 arranged and disposed to receive an interface cable 104. Interface cable 104 may be electrically connected with a guide wire receptacle 106 at a distal end 105 of interface cable 104. Interface cable 104 is arranged and disposed to electrically connect with a guide wire 108 by guide wire receptacle 106. Guide wire 108 is arranged and disposed for measuring internal conditions by a sensor 110 at an end 107 of guide wire 108. Interface cable 104 may further include a plug 120 configured for electrical communication with monitoring and control device 102. Alternatively, interface cable 104 may be hard-wired directly into monitoring and control device 102 at an end 103, or other means of electrical connection may be used.

Interface cable 104 may be any flexible multi-conductor shielded cable with an insulated covering. It is desirable that a shielded portion of interface cable 104 be connected to a shielded portion of guide wire receptacle 106. Interface cable 104 is arranged and disposed for an electronic communication signal to be provided through interface cable 104 to monitoring and control device 102. Guide wire receptacle 106 is arranged and disposed for an interconnector 112 of guide wire 108 to be releasably inserted into guide wire receptacle 106. Interconnector 112 includes a plurality of axial conductive portions 116 and a plurality of axial dielectric portions 118. The number of axial conductive portions 116 and axial dielectric portions 118 corresponds with the number of contacts inside guide wire receptacle 106. In the exemplary embodiment, each of interconnector 112 and guide wire receptacle 106 includes axial conductive portions 116, although in other embodiments more or fewer axial conductive portions 116 may be provided. Interconnector 112 is depicted as a hypo tube but may be any suitable device with a plurality of axial dielectric portions and a plurality of axial conductive portions.

Interconnector 112 is configured to be removably inserted into an aperture 201 of guide wire receptacle 106. Sensor 110 at end 107 of guide wire 108 may be inserted into a human body (e.g. intravenously), thereby permitting measurements from inside the body to be transmitted as electrical signals through guide wire 108 into guide wire receptacle 106 to interface cable 104 in electrical communication with monitoring and control device 102.

Sensor 110 of guide wire 108 may be inserted into the human body within a balloon catheter 114 or other manners known in the art. It is desirable that the method of inserting sensor 110 of guide wire 108 into the human body permit accurate and consistent measurements of conditions inside the body. As such, it is desirable that sensor 110 be inserted into a closed area with little external stimulus. For example, sensor 110 may be inserted into the femoral artery. As illustrated in the embodiment in FIG. 1, once guide wire 108 is inserted into the desired location, catheter 114 may be inserted onto guide wire 108.

Figure 2:
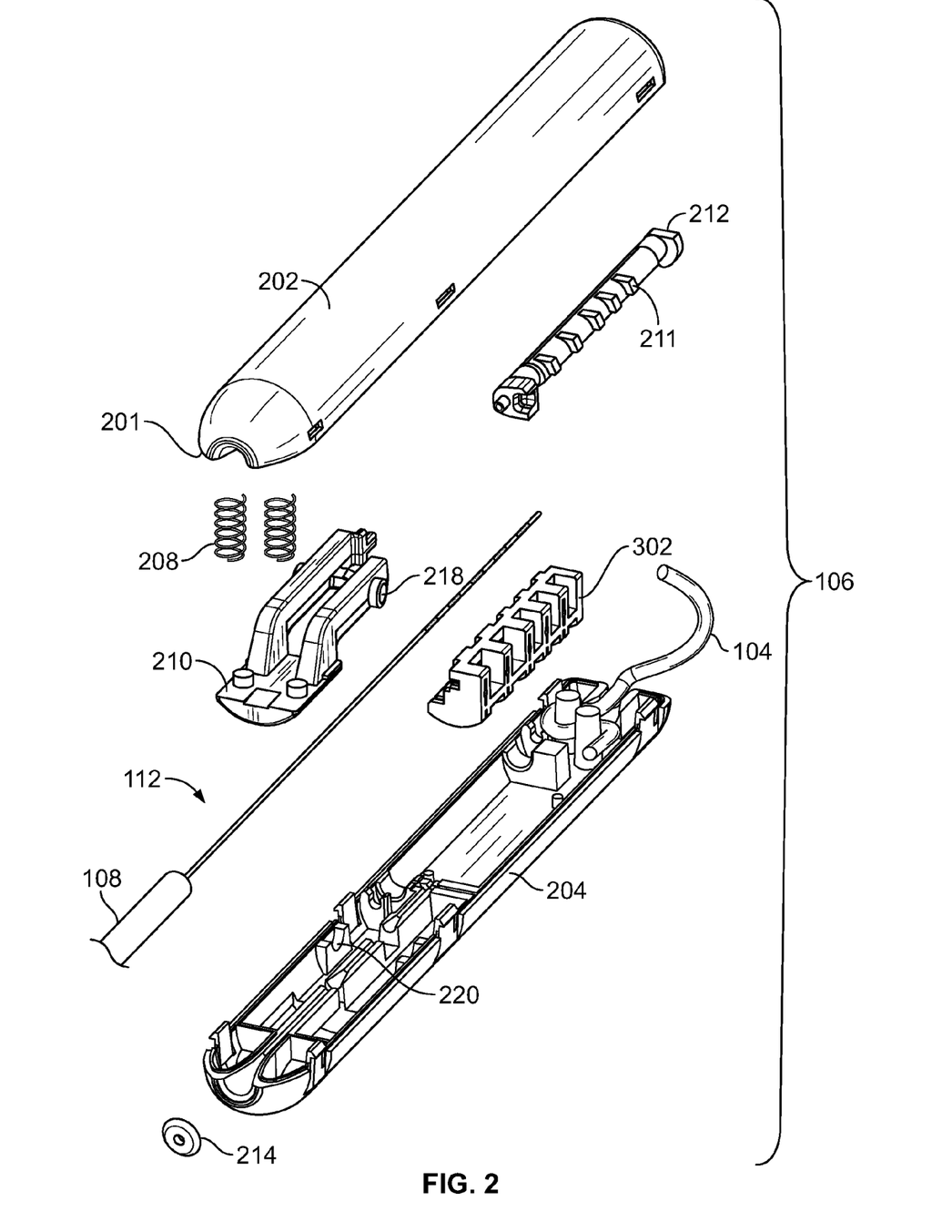
FIG. 2 illustrates an exploded view of an exemplary embodiment of a guide wire receptacle according to the disclosure.

Referring to FIG. 2, guide wire receptacle 106 is a connector that includes a body 200 (see FIG. 1) formed by a shielded upper housing 202 and a shielded lower housing 204. Shielded upper housing 202 is arranged to be secured to shielded lower housing 204 to form body 200, thereby protecting components housed within guide wire receptacle 106. Body 200 may be a molded interconnection device as known in the art.

Referring still to FIG. 2, guide wire receptacle 106 is arranged and disposed to receive guide wire 108 through aperture 201, which may be partially formed by shielded upper housing 202 and shielded lower housing 204. Shielded lower housing 204 may receive springs 208, a cam actuator 210, a cam 212, and a contact module 302 that may be electrically connected to interface cable 104. As illustrated in FIG. 2, interconnector 112 of guide wire 108 may be inserted into guide wire receptacle 106. Cam actuator 210 includes a fulcrum 218 configured to rest in a receiving slot 220 of shielded lower housing 204. Receiving slot 220 is arranged and disposed for receiving fulcrum 218.

Upon interconnector 112 being inserted into guide wire receptacle 106, cam actuator 210 may be engaged by the user thereby reducing or eliminating the force required to insert interconnector 112. As will be appreciated by those skilled in the art, guide wire receptacle 106 may be a zero insertion force connector. This reduction or elimination of the force required to insert interconnector 112 reduces the risk of breaking or damaging it. The engaged cam actuator 210 compresses springs 208 and rotates cam 212, thereby rotating lobes 211 on cam 212. When rotated, lobes 211 engage the contacts in a contact module 302, thereby permitting insertion of interconnector 112 into contact module 302. When interconnector 112 is fully inserted into contact module 302, the user may release pressure on cam actuator 210. The release of pressure permits springs 208 to expand. When springs 208 expand, cam actuator 210 rotates thereby rotating cam 212 in the opposite direction. When cam 212 rotates, lobes 211 on cam 212 rotate, thereby disengaging the contacts in contact module 302, which places the contacts in electrical communication with interconnector 112. Fully inserted interconnector 112 permits multiple separate signals to be transmitted and received between sensor 110 and the contacts.

FIG. 2 further illustrates guide wire receptacle 106 including an elastomeric guide seal 214. Guide seal 214 is arranged and disposed for interconnector 112 to be inserted through it, thereby preventing fluids from entering guide wire receptacle 106 and disrupting electrical communication. It is desirable that guide seal 214 include an opening slightly smaller than interconnector 112 that will expand upon insertion of interconnector 112 to substantially prevent contaminants, such as blood or other fluids, from entering guide wire receptacle 106. Additionally, guide seal 214 should be configured to permit insertion of interconnector 112 without damaging it. In other embodiments, the guide seal may be a wiper having a top and bottom portion configured to abut each other. The wiper may be a single unitary piece with a slot or aperture configured for insertion of the interconnector. Alternatively, the wiper may include separate pieces that abut each other but are configured for insertion of the interconnector. As will be appreciated by those skilled in the art, the top and bottom portions may have any suitable geometry including, but not limited to, half circles forming a disc, wedge-like portions, and brush-like components. The guide seal may be comprised of any suitable material including, but not limited to, elastomeric material, foam, plastic, and fabric. Additionally or alternatively, the guide seal may require that it is punctured by a pin prior to insertion of the interconnector.

Figure 3:
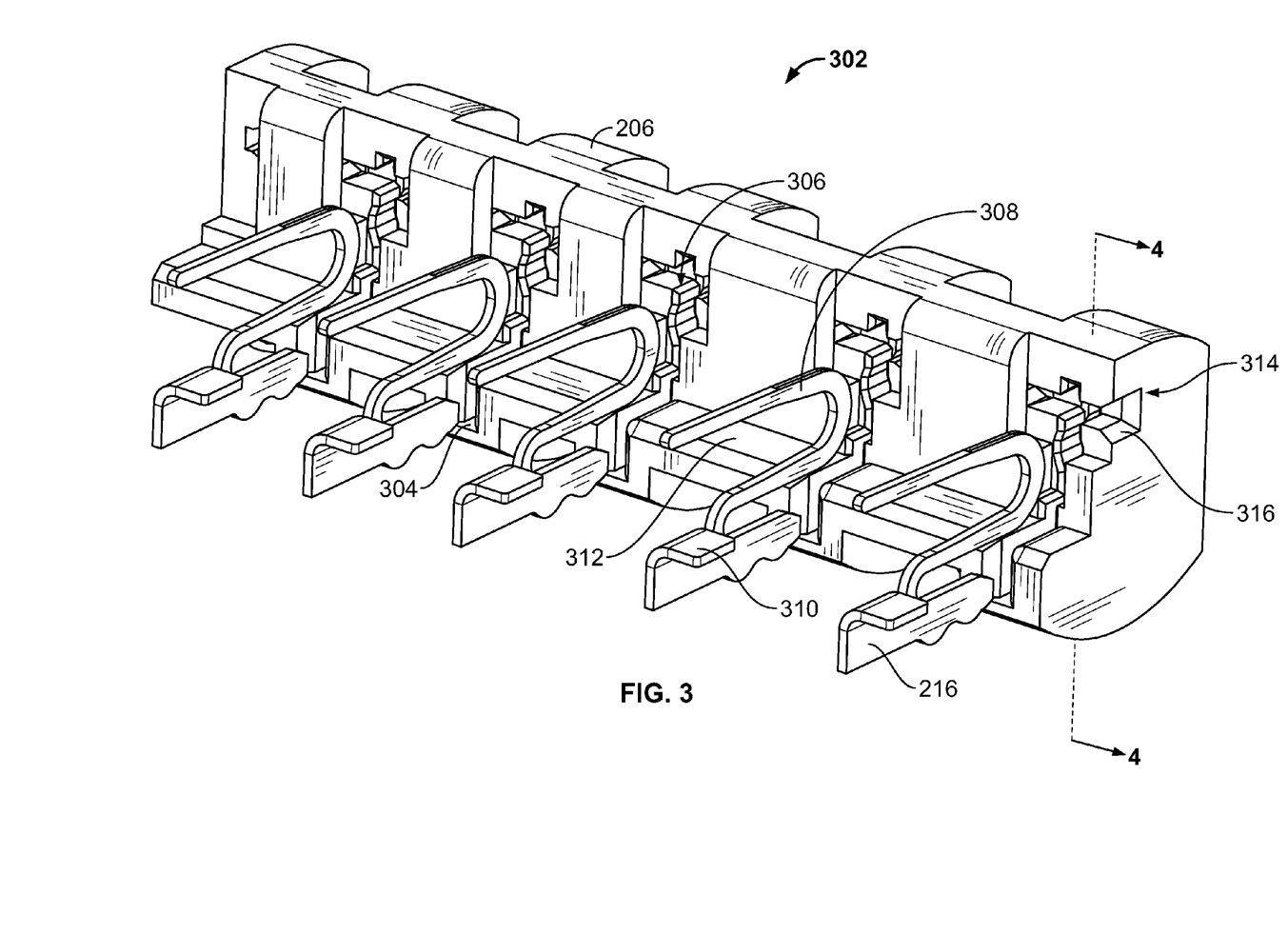
FIG. 3 illustrates an exploded view of an exemplary embodiment of a contact module including a contact housing and contacts according to the disclosure.

FIG. 3 illustrates an exemplary embodiment of contact module 302. As illustrated in FIG. 3, contact module 302 includes contact housing 206 and contacts 216. Contact housing 206 may be comprised of a dielectric material. Contacts 216 may be comprised of a conductive material. Contact housing 206 may include grooves 304 arranged and disposed to retain contacts 216. Contact housing 206 may also include guides 306 arranged and disposed for an upper portion 308 to insert into contact housing 206. Additionally, contact 216 may include a terminal 310 providing a conductive surface for receiving a conductive wire (not shown) by crimping, clipping, soldering, or otherwise attaching the wire to the conductive surface of terminal 310. Terminal 310 may also provide lateral support to contacts 216 upon being inserted into contact housing 206. As illustrated in FIG. 3, terminal 310 may be a substantially planar surface that engages a contact housing surface 312 upon contacts 216 being inserted into contact housing 206.

Contact housing 206 may include a feature 314 configured to receive interconnector 112. Feature 314 may include chamfers 316 for increased ease in inserting interconnector 112 into contact housing 206. Contact housing 206 may be further configured to permit the interconnector to be inserted through contact housing 206, thereby establishing electrical contact between contacts 216 and axial conductive portions 116 of interconnector 112. Feature 314 may be a channel extending through at least a portion of contact housing 206. Feature 314 may extend through the entire contact housing or may be defined by an interior surface of contact housing 206, limiting the extent that interconnector 112 may be inserted into contact module 302.

Figure 4:
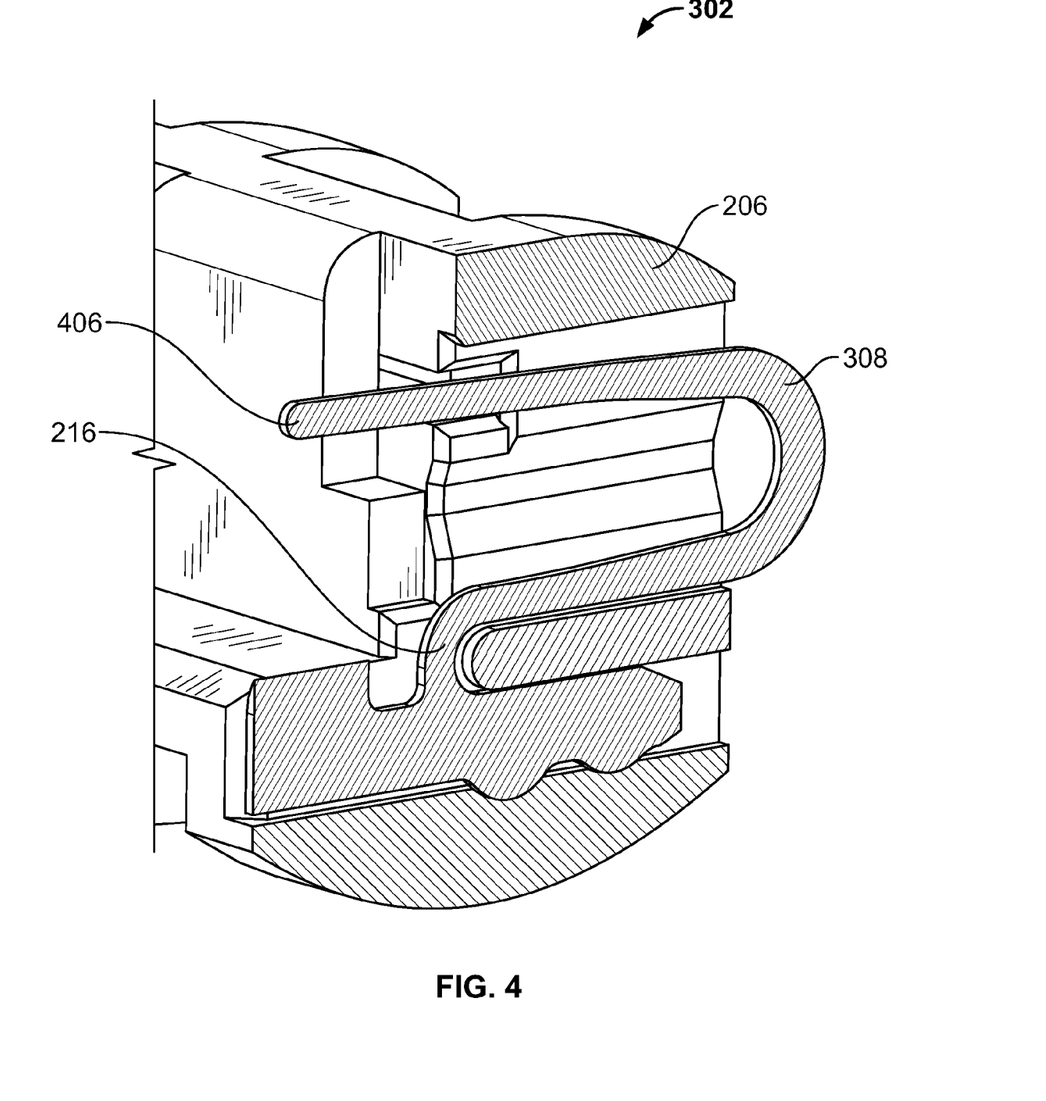
FIG. 4 illustrates a sectional view of the contact housing in FIG. 3 along a line 4-4 with contacts inserted into the contact housing.
Figure 5:
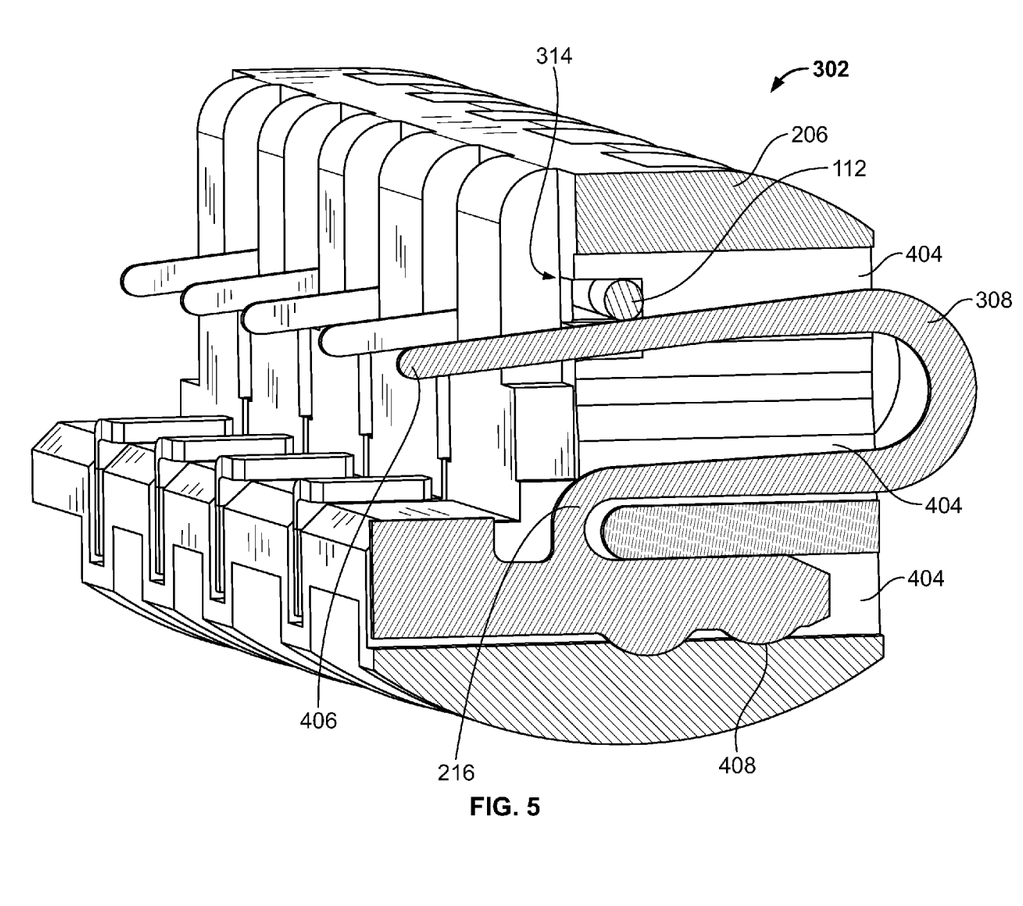
FIG. 5 illustrates a sectional view of the contact housing in FIG. 3 along a line 4-4 with contacts inserted into the contact housing and an interconnector inserted into the contact module.

Referring next to FIG. 4, contact module 302 may include contact 216 inserted into contact housing 206. Upper portion 308 of contact 216 may be arranged and disposed to flex. The ability of upper portion 308 to flex may permit an end portion 406 of contact 216 to be moved substantially vertically by being engaged by a mechanism, such as cam 212 (see FIG. 2). Cam 212 may engage end portion 406 of contact 216 by providing a force upon end portion 406 thereby flexing upper portion 308. When upper portion 308 is flexed, end portion 406 reveals feature 314 (see FIG. 3), thereby permitting the interconnector to be inserted into feature 314. As illustrated in FIG. 5, feature 314 may be filled with the interconnector. Upon the mechanism disengaging end portion 406 of contact 216, upper portion 308 flexes in the reverse direction thereby resulting in contact 216 providing a normal force on the interconnector. The ability to flex also permits normal force to provide a tight fit between the interconnector and contact module 302. In one embodiment, the interconnector is substantially circumferentially supported and secured by contact housing 206 and/or contact 216. In part, the support is provided by feature 314 in contact housing 206 providing a support surface for the interconnector. The support surface provides support in the opposite direction of the normal force applied by contact 216 to interconnector 112.

Figure 6:
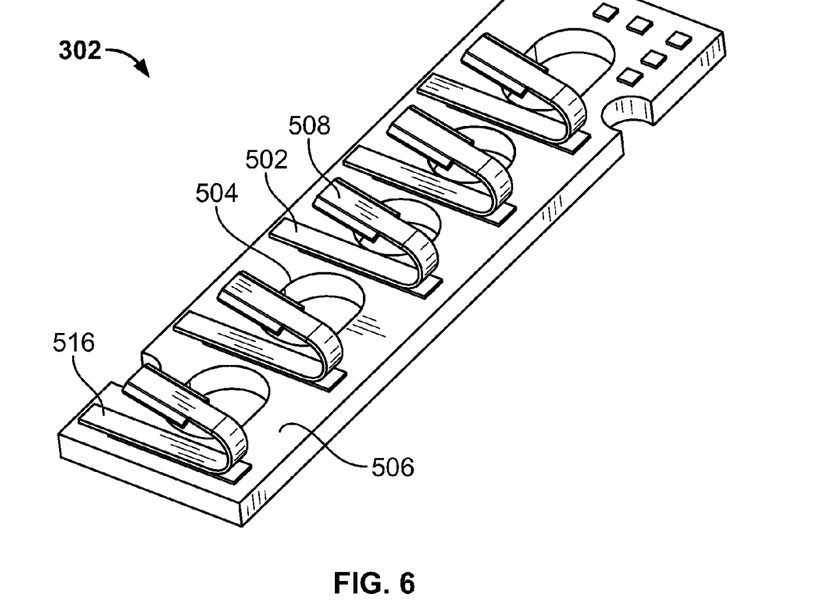
FIG. 6 illustrates an alternate exemplary embodiment of a contact module according to the disclosure.

Referring to FIG. 5, the contact housing of contact module 302 additionally secures contacts 216. The contact housing may include grooves 404 arranged at a size slightly larger than contact and disposed to substantially prevent movement of contact (except for flexing where applicable). Additionally, contact 216 may include retention features 408 to prevent contact 216 from being removed from the contact housing FIG. 6 illustrates another exemplary embodiment of contact module 302. In the embodiment of FIG. 6, contact module 302 includes printed wiring board 506 with contacts 516 affixed to printed wiring board 506. The substrate includes holes 504 arranged and disposed for housing towers (not shown) to be inserted through. The housing towers in conjunction with holes 504 may secure contact module 302 to shielded lower housing 204. Contact 516 is formed from a single integrated conductive band having a flexible upper portion 508. Lower portion 502 of contact 516 may be affixed to printed wiring board 506. Contacts 516 are secured within printed wiring board 506. Contacts 516 may be affixed by mechanical force, adhesive, and/or solder.

Figure 7:
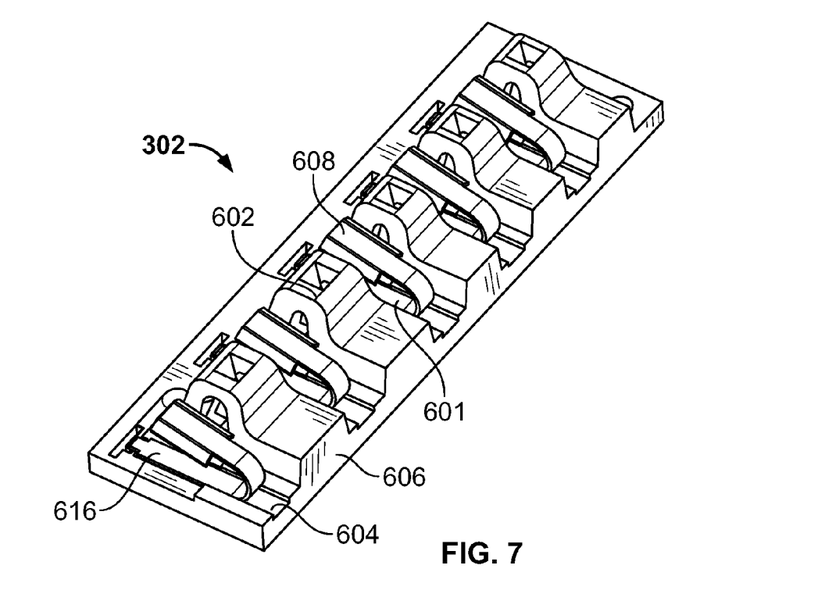
FIG. 7 illustrates another alternate embodiment of a contact module according to the disclosure.

FIG. 7 illustrates another exemplary embodiment of contact module 302. In the embodiment of FIG. 7, contact module 302 includes contact housing 606 as a structure with grooves 604 configured to align and receive contacts 616. Lower portion 601 of contact 616 is arranged and disposed for being affixed to contact housing 606. Contacts 616 may be secured by mechanical force, adhesive, and/or solder. Contact housing 606 further includes upper features 602. Upper feature 602 is configured to guide, secure, and support the interconnector. Upper feature 602 may abut a corresponding actuator (not shown), such as cam actuator 210 (see FIG. 2) and/or cam 212 (see FIG. 2). Contact 616 is a single integrated conductive band with a flexible upper portion 608.

Figure 8:
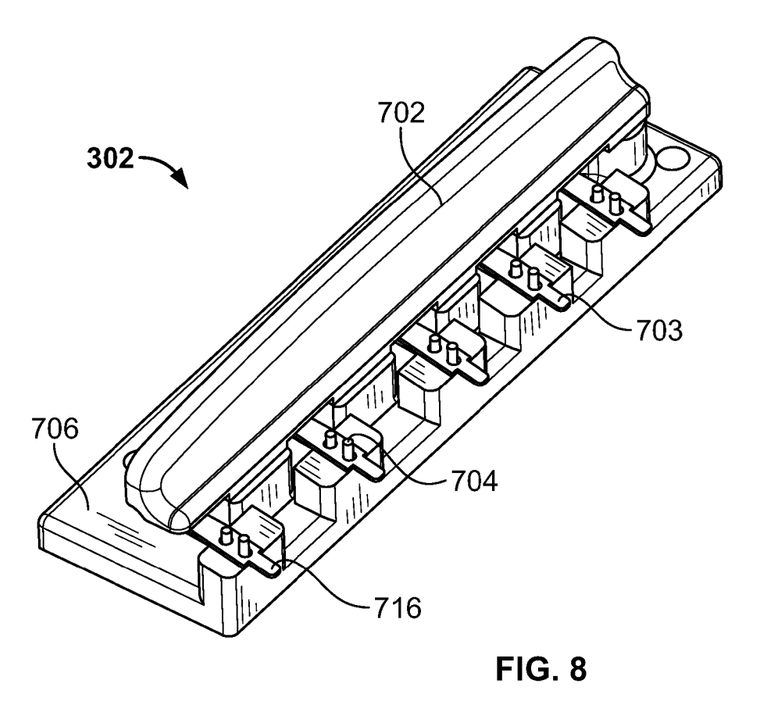
FIG. 8 illustrates still another alternate embodiment of a contact module according to the disclosure.

FIG. 8 illustrates another exemplary embodiment of contact module 302. In the embodiment of FIG. 8, contact module 302 includes contact housing 706 as a substrate configured for receiving contacts 716. As illustrated, contacts 716 are secured by interface fit pins 704, which may be ultrasonically welded. Contacts 716 may be partially or entirely secured by a contiguous dielectric shell 702. Contiguous dielectric shell 702 may provide support to interconnector 112 in opposition to the normal force provided by contacts 716. As illustrated, contacts 716 can include terminal 703 providing a conductive surface for receiving a conductive wire (not shown).

Figure 9:
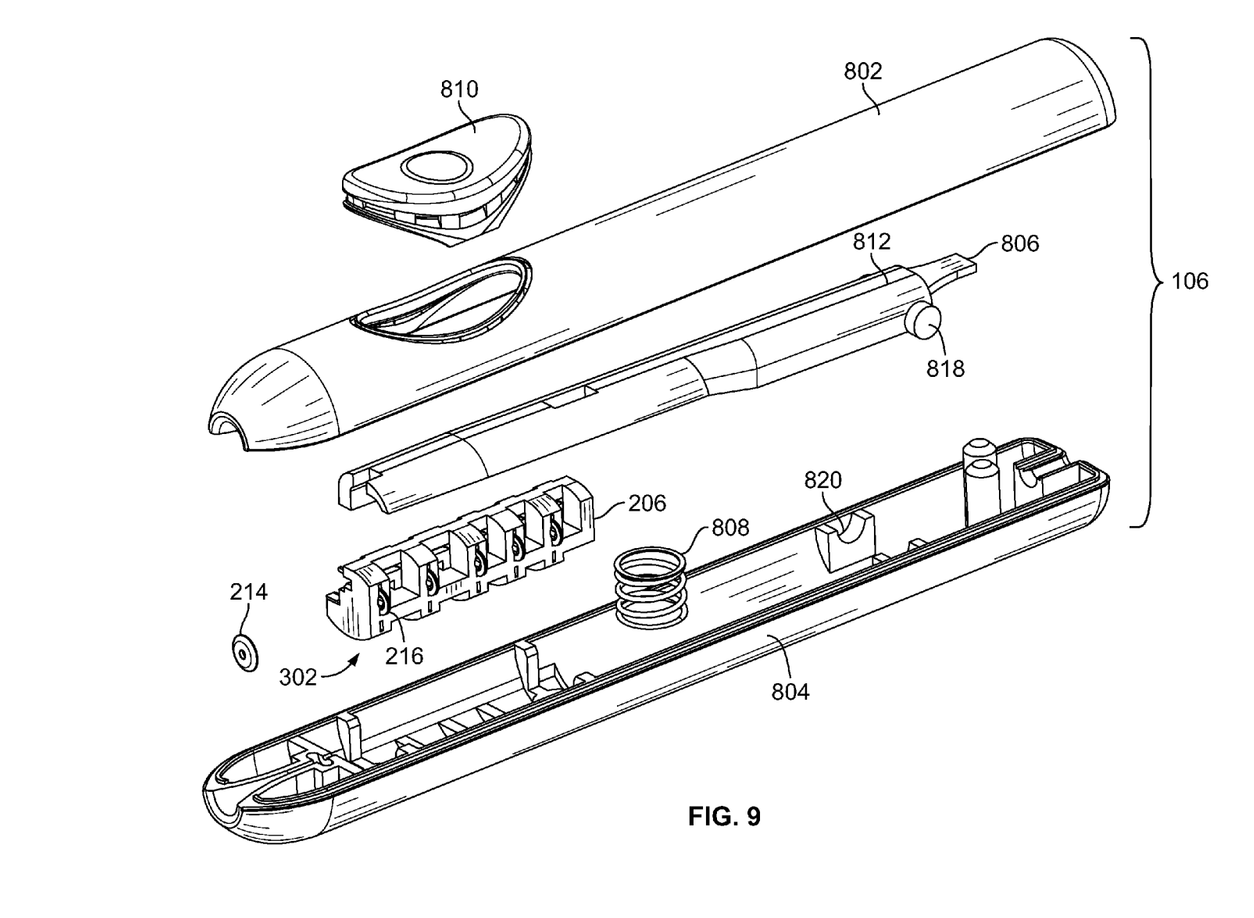
FIG. 9 illustrates an alternate embodiment of a guide wire receptacle according to the disclosure.

FIG. 9 illustrates an alternate embodiment of guide wire receptacle 106. In the embodiment of FIG. 9, guide wire receptacle 106 includes a shielded upper housing 802 and a shielded lower housing 804. Shielded upper housing 802 may be secured to shielded lower housing 804, thereby protecting components housed within guide wire receptacle 106. Shielded lower housing 804 and shielded upper housing 802 are comprised of a dielectric material. Both housings 802, 804 are configured to receive the guide wire (not shown), the interconnector (not shown), cam 812, spring 808, and contact module 302 that is in electrical communication with interface cable (not shown). The interconnector may be inserted into guide wire receptacle 106.

Referring still to FIG. 9, while the interconnector is being inserted into guide wire receptacle 106, cam actuator 810 may be manually engaged thereby reducing or eliminating the force required to insert the interconnector. This reduction or elimination of the force required to insert the interconnector reduces the risk of breaking or damaging the interconnector. The engaged cam actuator 810 compresses spring 808. When spring 808 is compressed, cam 812 partially rotates along a fulcrum 818 configured to rest in receiving slot 820 of both housings 802, 804. When rotated, cam actuator 810 engages contacts 216 thereby permitting insertion of the interconnector into contact module 302. When the interconnector is fully inserted into contact module 302, cam actuator 810 may be disengaged thereby permitting spring 808 to expand. When spring 808 expands, cam 812 rotates in the opposite direction. When cam 812 rotates and disengages contacts 216, contacts 216 may engage the interconnector in contact housing 206, thereby permitting contacts 216 to be in electrical communication with the interconnector. The fully inserted interconnector permits multiple separate signals to be transmitted and received between a sensor and contacts 216. Additionally, cam 812 may include a tab 806 that may be used for disengaging contacts 216. In another embodiment, spring 808 is not included and tab 806 or other feature on cam 812 is used to disengage contacts 216. In yet another embodiment, spring 808 is included and tab 806 is not included. As depicted in FIG. 9, cam 812 may be a button lever and cam actuator 810 may be a button lever actuator.

Figure 10:
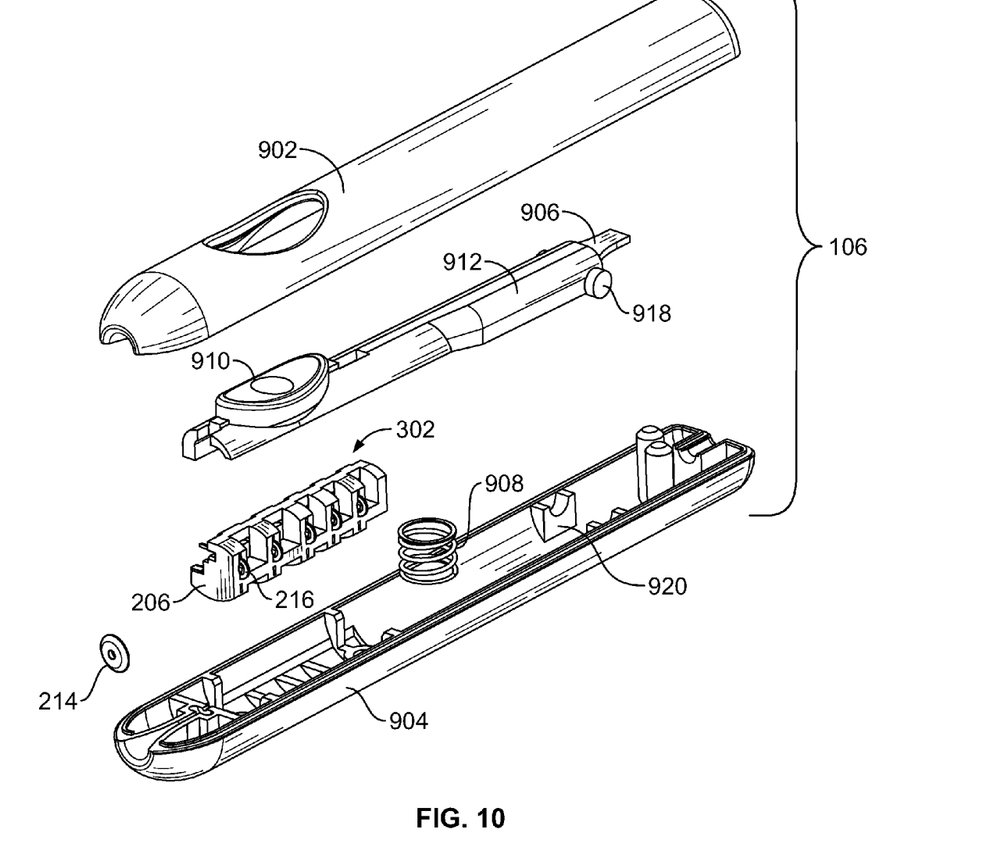
FIG. 10 illustrates another alternate embodiment of a guide wire receptacle according to the disclosure.

FIG. 10 illustrates an alternate embodiment of guide wire receptacle 106. In the embodiment in FIG. 10, guide wire receptacle 106 includes a shielded upper housing 902 and a shielded lower housing 904. Shielded upper housing 902 may be secured to shielded lower housing 904, thereby protecting components housed within guide wire receptacle 106. Shielded upper housing 902 and shielded lower housing 904 are comprised of a dielectric material. Both housings 902, 904 are configured to receive the guide wire (not shown), the interconnector (not shown), cam 912, spring 908, and contact module 302, which is in electrical communication with the interface cable (not shown).

Referring still to FIG. 10, when the interconnector is being inserted into guide wire receptacle 106, cam actuator 910 may be manually engaged thereby reducing or eliminating the force required to insert the interconnector. This reduction or elimination of the force required to insert the interconnector reduces the risk of breaking or damaging the interconnector. In the embodiment illustrated by FIG. 10, cam actuator 910 is a protruding portion of cam 912. The engaged cam 912 compresses spring 908. When spring 908 is compressed, cam 912 rotates along a fulcrum 918 configured to rest in receiving slot 920 formed by both housings 902, 904. When rotated, cam 912 engages contacts 216 thereby permitting insertion of the interconnector into contact module 302. When the interconnector is fully inserted into contact module 302, cam actuator 910 may be disengaged, thereby permitting spring 908 to expand. When spring 908 expands, cam 912 rotates in the opposite direction. When cam 912 rotates and disengages contacts 216, contacts 216 may engage the interconnector in contact housing 206, thereby permitting contacts 216 to be in electrical communication with the interconnector. The fully inserted interconnector permits multiple separate signals to be transmitted and received between a sensor (not shown) and contacts 216. In another embodiment, spring 908 is not included and the tab or other feature on cam 912 is used to disengage contacts 216 instead of cam actuator 910 to remain depressed for contacts 216 to be engaged. In yet another embodiment, both spring 908 and the tab (or other feature on cam 912) are included. Additionally, cam 912 may include a tab 906 that may be used for disengaging contacts 216. In another embodiment, spring 908 is not included and tab 906 or other feature on cam 912 is used to disengage contacts 216. In yet another embodiment, spring 908 is included and tab 906 is not included. As depicted in FIG. 10, cam 912 may be a button lever and cam actuator 910 may be a button lever actuator protruding from the button lever.

Figure 11:
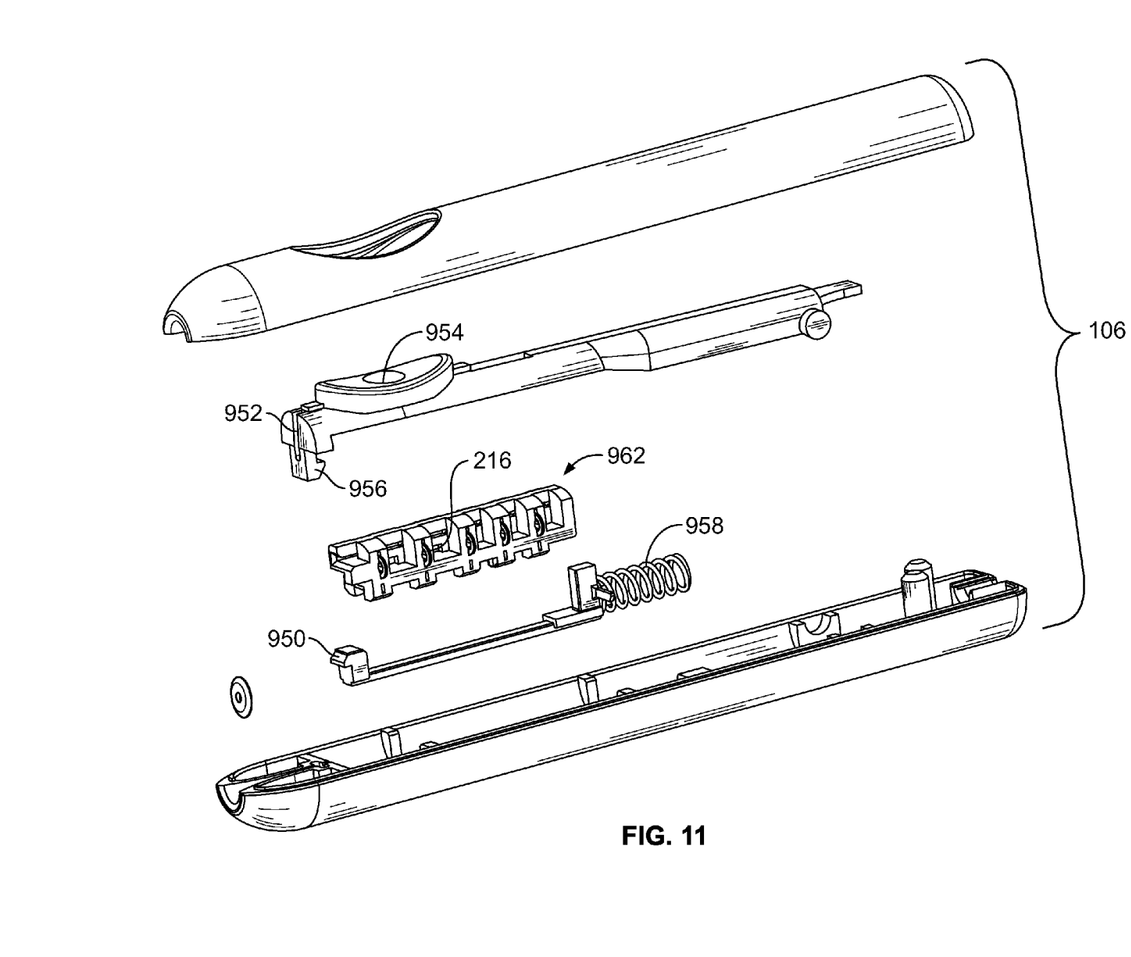
FIG. 11 illustrates another alternate embodiment of a guide wire receptacle according to the disclosure.

Referring to FIG. 11, another embodiment of the present disclosure includes a latching member 950 arranged and disposed for releasably securing cam 952 after cam 952 engages contacts 216. When cam actuator 954 is depressed, cam 952 may engage contacts 216 as described above. When contacts 216 are engaged, a latch catch 956 on cam 952 is pushed against latching member 950. As depicted in FIG. 11, latching member 950 and latch catch 956 may have angled corresponding geometry. This angled corresponding geometry permits a downward force to be applied to cam 952 (directly or through a cam actuator as described above) and, therefore, latch catch 956. When latch catch 956 contacts latching member 950, the angled corresponding geometry permits latch catch 956 to provide an axial force onto latching member 950. The axial force applied to latching member 950 compresses a latch spring 958. After latch catch 956 is pushed below the angled corresponding geometry of latching member 950, latch spring 958 may expand thereby pushing latching member 950 axially in the reverse direction. At this point, an audible clicking sound may result. When latching member 950 is axially pushed by latch spring 958 in this reverse direction, latching member 950 secures cam 952 while cam 952 engages contacts 216. This continued engaging of contacts 216 permits the user of guide wire receptacle 106 to release cam actuator 954 without cam 952 disengaging contacts 216. As described above, when cam 952 engages contacts 216, the interconnector may be inserted into guide wire receptacle 106.

Referring again to FIG. 11, when the interconnector is fully inserted into contact module 962, the interconnector applies an axial force to latching member 950. The axial force applied to latching member 950 compresses latch spring 958 thereby moving latching member 950 axially. In one embodiment, the axial force may be provided by the interconnector contacting the end of feature 314 permitting the interconnector to push against the contact housing in an axial direction. In another embodiment, the axial force may be provided by the interconnector reaching a mechanism that provides axial force. In yet another embodiment with the feature extending entirely through the contact housing, axial force may be provided when interconnector 112 extends through the entire contact housing. Referring to FIG. 11, when latching member 950 is moved axially, latching member 950 releases latch catch 956, thereby resulting in cam 952 disengaging contacts 216. As described above, when cam 952 disengages contacts 216, the interconnector and contacts 216 may be in electrical communication. At this point, an audible clicking sound may result. As depicted in FIG. 11, cam 952 may be a button lever and cam actuator 954 may be a button lever actuator protruding from the button lever.

Figure 12:
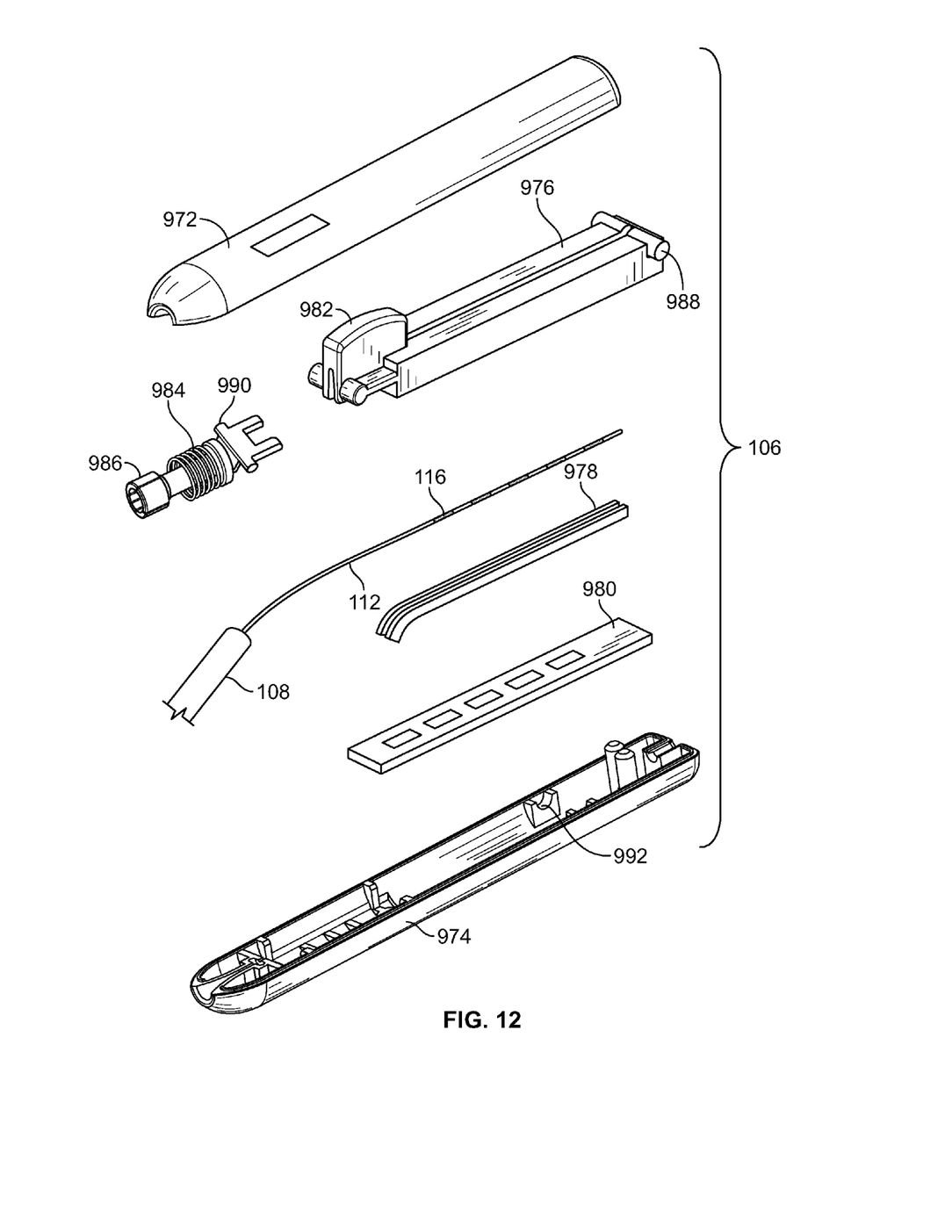
FIG. 12 illustrates another alternate embodiment of a guide wire receptacle according to the disclosure.

FIG. 12 illustrates an alternate embodiment of guide wire receptacle 106. In the embodiment of FIG. 12, guide wire receptacle 106 includes a shielded upper housing 972 and a shielded lower housing 974. Shielded upper housing 972 may be secured to shielded lower housing 974, thereby protecting components housed within guide wire receptacle 106. Shielded lower housing 974 is configured to receive interconnector 112, a cam 976, an anisotropic material 978, and a printed circuit board 980.

In the embodiment illustrated by FIG. 12, anisotropic material 978 acts as the plurality of contacts and printed circuit board 980 acts as the contact housing. As will be appreciated by those skilled in the art, an anisotropic material is a material with differing effects for compression in one direction as opposed to another direction. The differing effect permits the material to be compressed in a vertical or z-axis thereby permitting conductivity. Anisotropic materials are also described as z-axis materials and include, but are not limited to, arrays of wires, silver flakes in a polymer, molded particle interconnect, interposers with contacts embedded in a matrix, and/or polyamid compression sheets. Anisotropic material 978 permits electrical signals to be transmitted in compressed portions. The compressed portions permit electrical communication by forming an electrically conductive region in the compressed portions while remaining dielectric in non-compressed portions. The portions that are not compressed do not permit electrical signals to be transmitted. In FIG. 12, anisotropic material 978 and printed circuit board 980 constitute the contact module.

Referring to FIG. 12, when interconnector 112 is being inserted into guide wire receptacle 106, a cam actuator 982 may be manually engaged thereby reducing or eliminating the force required to insert interconnector 112. This reduction or elimination of the force required to insert interconnector 112 reduces the risk of breaking or damaging interconnector 112. The engaged cam actuator 982 compresses a spring 984 in a collett 986. When spring 984 is compressed, cam 976 partially rotates along a fulcrum 988 configured to rest in receiving slot 992 of shielded lower housing 974 of guide wire receptacle 106. When partially rotated, cam 976 is secured in a depressed position by a securing mechanism 990 connected to collett 986. In the depressed position, cam 976 compresses anisotropic material 978. Anisotropic material 978 is arranged and disposed for receiving interconnector 112 and to be received by printed circuit board 980. In one embodiment, anisotropic material 978 includes a channel extending in the axial direction arranged and disposed to slidably receive interconnector 112 prior to cam 976 being depressed. When cam 976 is depressed and interconnector 112 is positioned within anisotropic material 978, electrical signals from axial conductive portions 116 of interconnector 112 may be transmitted to printed circuit board 980. Fully inserted interconnector 112 permits multiple separate signals to be transmitted and received between sensor 110 and printed circuit board 980. As depicted in FIG. 12, cam 976 may be a button lever and cam actuator 982 may be a button lever actuator protruding from the button lever.

In the embodiment of FIG. 12, when interconnector 112 is fully inserted into anisotropic material 978, if cam actuator 982 is depressed, securing mechanism 990 disengages cam 976 and expands spring 984 on collett 986 thereby resulting in cam 976 no longer applying pressure to anisotropic material 978. With no pressure being applied to anisotropic material 978, no electrical signals are transmitted to printed circuit board 980.

While the disclosure has been described with reference to a preferred embodiment, it will be understood by those skilled in the art that various changes may be made and equivalents may be substituted for elements thereof without departing from the scope of the disclosure. For instance, the materials disclosed as comprising the embodiments are exemplary and not exhaustive. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. An electrical connector comprising: a body arranged and disposed to receive an interconnector of a guide wire at a first end and an interface cable at a second end;
    a contact module in the body, the contact module comprising a contact housing and a plurality of contacts, disposed in the contact housing, the plurality of contacts being configured for electrical connection with the interface cable and the guide wire; and
    a cam actuator and a cam in the body, the cam actuator arranged and disposed for partially rotating the cam,
    wherein the interconnector comprises a plurality of axial conductive portions separated by a plurality of axial dielectric portions, the number of the axial conductive portions corresponding to the number of the contacts in the contact module,
    the interface cable is arranged and disposed for electrically connecting with a monitoring and control device, and
    the cam being arranged and disposed for engaging the contacts upon being partially rotated, the engagement flexing each one of the contacts within the contact module to permit the interconnector to be inserted into the contact module,
    wherein the cam actuator is arranged and disposed to be manually engaged by depressing said cam actuator, thereby permitting the interconnector to be inserted into the body, the cam actuator further arranged and disposed for adjusting the cam upon being depressed, the cam including a fulcrum configured to rest in a receiving slot of the body, the receiving slot arranged and disposed for receiving the fulcrum thereby permitting the cam to partially rotate upon the cam actuator being engaged.

2. The electrical connector of claim 1, wherein the electrical connector is arranged and disposed for releasably receiving the guide wire.

3. The electrical connector of claim 1, wherein the cam actuator being a protruding portion of the cam, the cam actuator arranged and disposed for adjusting the cam upon being depressed.

4. The electrical connector of claim 1, wherein the contact housing comprises:
    grooves arranged and disposed for the contacts to slide into the grooves; and
    recessed portions arranged and disposed to receive an upper portion of the contacts, the contacts comprising terminals providing a conductive surface for electrical connection, the upper portion arranged and disposed to flex upon being engaged by a cam, thereby permitting the interconnector to be inserted into the contact module.

* * * * *